United States Patent [19]

Duchars et al.

[11] Patent Number: 6,136,567
[45] Date of Patent: Oct. 24, 2000

[54] PRODUCTION OF PROTEINS, PLASMIDS CODING THEREFOR AND ORGANISMS CONTAINING SUCH PLASMIDS

[75] Inventors: Matthew Guy Duchars, Darlington; Andrew William Topping, Richmond, both of United Kingdom

[73] Assignee: Zeneca Limited, United Kingdom

[21] Appl. No.: 09/125,604

[22] PCT Filed: Feb. 20, 1997

[86] PCT No.: PCT/GB97/00465

§ 371 Date: Aug. 21, 1998

§ 102(e) Date: Aug. 21, 1998

[87] PCT Pub. No.: WO97/31118

PCT Pub. Date: Aug. 28, 1997

[30] Foreign Application Priority Data

Feb. 22, 1996 [GB] United Kingdom .................. 9603803

[51] Int. Cl.[7] ..................................................... C12P 21/04
[52] U.S. Cl. ....................... 435/71.2; 485/69.1; 485/71.1; 485/183; 485/252.3; 485/252.33; 485/320.1; 485/440; 485/471; 485/476
[58] Field of Search ................................ 435/69.1, 320.1, 435/252.3, 252.33, 440, 471, 476, 183, 71.1, 71.2

[56] References Cited

U.S. PATENT DOCUMENTS 5,017,488  5/1991  McAllister et al. ..................... 435/194
5,460,954  10/1995  Lee et al. ............................... 435/69.4

FOREIGN PATENT DOCUMENTS

WO89/00605  1/1989  WIPO .

OTHER PUBLICATIONS

Moreau et al., Canadian Journal of Microbiology 38(4):267–357 (1992).

New England Biolabs Catalog 1995. New England Biolabs, Inc. Beverly, MA., pp. 216–217.

Kellett, et al: "Xylanase B and an arabinofuranosidase from *Pseudomonas fluorescene subsp. cellulosa* contain identical cellulose–binding domains and are encoded by adjacent genes", Biochem. J. (1990) 272:369–376.

Barth, et al: "Cloning and Partial Sequencing of an Operon Encoding Two *Pseudomonas putida* Haloalkanoate Dehalogenases of Opposite Stereospecificity", J. Bacteriology (1992) 174:2612–2619.

Weyer, et al: "A baculovirus dual expression vector derived from the *Autographa califonica* nuclear polyhedrosis virus polyhedin and p10 promoters: co–expression of two influenza virus genes insect cells", Journal of General Virology (1991), 72: 2967–2974.

Caunt, et al: "Stability of recombinant plasmids in yeast", Journal of Biotechnology (1988) 8: 173–192.

*Primary Examiner*—Remy Yucel
*Attorney, Agent, or Firm*—Cushman Darby & Cushman, IP Group of Pillsbury Madison & Sutro LLP

[57] ABSTRACT

Plasmids which comprise: (1) an origin of replication; (2) an additional sequence required for plasmid replication or preferably a gene giving a selective advantage; and (3) two expression cassettes each of which are located between (1) and (2) but are separated by (1) and (2) from each other; and which are free from inverted repeat sequences (other than in (3)) are highly persistent though successive generations of microbes containing them.

14 Claims, 4 Drawing Sheets

SEQUENCE LISTING

<160> NUMBER OF SEQ ID NOS: 5

<210> SEQ ID NO 1
<211> LENGTH: 10
<212> TYPE: DNA

-continued

```
<213> ORGANISM: Artificial Sequence
<220> FEATURE:
<223> OTHER INFORMATION: Description of Artificial Sequence:oligonucleotide

<400> SEQUENCE: 1
ggccctgcag                                                              10

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 2
ctggatcccg gcgttttcag gctttgctc                                         29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 3
acagatcttc accgaccaca ataatccgc                                         29

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 4
acagatcttg accctgtgcg agaaactg                                          28

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 5
tgggatccgc tcggcgttta cttcttcca                                         29
```

PRODUCTION OF PROTEINS, PLASMIDS CODING THEREFOR AND ORGANISMS CONTAINING SUCH PLASMIDS

This application is the national phase of international application PCT/ GB97/00465 filed Feb. 20, 1997 which designated the U.S.

BACKGROUND OF THE INVENTION

1. Field of the Invention

THIS INVENTION relates to the production of proteins, plasmids coding therefor and organisms containing such plasmids.

2. Background Information

It is known to modify microbes to produce desired proteins, for example enzymes, by incorporating plasmids coding for a desired protein into a microbe which would not otherwise produce it or which would not produce it in sufficient quantity. There is however a tendency for the plasmids to be lost on prolonged cultivation of the organism. It is believed that this is at least partly due to the production, on each division of the microbes, of a small number of daughter cells which contain none of the said plasmids and which are in consequence at a selective advantage over those which contain the desired plasmids. In the course of time, cells which contain none of the desired plasmids increase as a proportion of the total cells present.

In order to overcome this effect it is known to incorporate in the plasmid one or more genes which give a selective advantage to the microbe, for example genes giving resistance to an antibiotic are suitable if the microbes are cultivated in the presence of the antibiotic, or genes making good a deficiency in the host organism may be incorporated.

There is also a tendency for mutated variants of the plasmid which do not produce the desired protein to be produced for example by a mutation leading to the introduction of a stop codon in the gene or partial or complete deletion of the protein coding sequence. Microbes containing such mutated plasmids will tend to have a selective advantage compared with those having the original plasmid and the desired protein producing capability of the microbe may be reduced or lost on prolonged cultivation.

In DDR patent 233,851 A1 there are disclosed vector plasmids in which a sequence is present twice in opposite senses (inverted repeat sequences) into each of which sequences duplicate genes are cloned or recloned. This is said to cause increased synthesis of the gene product in the microorganism due to the gene dosage effect. The inverted repeat sequences must each have at least one homologous cleavage site into which the duplicate genes may be inserted. Stable plasmids are disclosed as producible.

SUMMARY OF THE INVENTION

Surprisingly we have now found that according to this invention stable plasmids can be produced from vectors which do not have inverted repeat sequences. This has important advantages.

Firstly, it reduces or eliminates the number of homologous cleavage sites and therefore the tendency to cut the plasmid into ineffective fragments in the process of cutting it to insert the desired gene. It is clear that each inverted sequence of DDR 233851 A1 must have at least one cleavage site and that these will be homologous. Normally the vector plasmids will be cleaved at both such sites. This increases the difficulty of constructing a plasmid with the desired gene correctly inserted into both of the inverted sequences. For example the free ends may link with a single added gene leaving plasmids with only one such gene. In addition non-functional nucleic acid fragments will be formed. The greater the number of cleavage sites in the inverted sequences the greater this problem becomes.

Secondly, it reduces the dangers of inter- and intra-plasmid recombination which can lead to scission of the plasmid. The presence of unnecessary DNA adjacent to the desired genes increases the likelihood of recombination leading to the loss of part or all of that gene. In addition, recombination between the inverted repeat sequences in different plasmid molecules (copies) may lead to formation of unstable multimeric plasmids.

By "Expression cassette" is meant a DNA sequence effective in production of a protein which comprises a promoter sequence and ribosomal binding site, a gene coding for a protein and normally a termination sequence. The gene may code for a fusion protein and may have a signal sequence.

Thirdly, it enables the production of smaller plasmids. We have found that according to our invention plasmids (excluding the desired expression cassette) of at most 10 kB, for example at most 6 kB and even for example at most 5 kB may be used. Each such plasmid places a smaller burden on the host organism than a larger plasmid. They normally also have higher copy numbers than larger plasmids for example 50–300 or even more than 300 plasmids per host cell with, in general, an improvement in output of the desired protein.

Fourthly, the inverted repeat sequences may themselves code for proteins thus placing an additional burden on the host and complicating separation of the desired product.

The invention comprises a continuous process for the production of organisms containing plasmids or polypeptides expressed by genes of such plasmids in which a plasmid comprises an origin of replication and an additional sequence required for plasmid replication and/or preferably a gene giving a microbe a selective advantage, and two expression cassettes each being in a DNA sequence located between the originating sequence and the gene giving the selective advantage or an additional sequence required for plasmid replication but being separated from one another on one side by DNA comprising the origin of replication and on the other side by DNA comprising the gene giving the selective advantage or the sequence required for plasmid replication, the plasmid being substantially free from inverted repeat sequences other than sequences represented by the expression cassettes.

If desired, additional expression cassettes may be included. The expression cassettes may be different but preferably are the same.

Preferably at most one antibiotic resistance gene is present.

Preferably the expression cassettes code for the same protein or for proteins which are enzymes used together for catalytic purposes whereby the organism or material derived therefrom is useful as a catalyst or a component of a catalyst comprising both such enzymes.

By "continuous process" is meant a process in which fresh nutrients are added and product removed continuously or intermittently without discontinuing the fermentation. Before operating a continuous process it is necessary to reach a suitable concentration of the organisms per unit volume of culture medium. It is normal to reach that condition by inoculation of a fermenter with the desired organism and permitting it to grow until the desired concentration is reached, and no product would normally be removed until then other than for sampling. It is preferred that at least 5, preferably at least 10 and more preferably at least 50 generations of organisms be produced after this has been achieved. Suitably a production of 5%, preferably 10% and more preferably at least 15% by weight of the desired protein is produced based on the total protein content of the organism.

The invention also comprises a plasmid which comprises an origin of replication and an additional sequence required for plasmid replication and/or preferably a gene giving a microbe a selective advantage, and two expression cassettes which express the same polypeptide or different polypeptides which are enzymes used for catalytic purposes and which are preferably the same, each being in a DNA sequence located between the origin of replication and the gene giving the selective advantage or the additional sequence required for plasmid replication but being separated from one another on one side by DNA comprising the origin of replication and on the other side by DNA comprising the gene giving the selective advantage or the additional sequence required for plasmid replication, the plasmid being substantially free from inverted repeat sequences other than sequences represented by the expression cassettes. A second gene giving a selective advantage may be present if desired as also may additional expression cassette(s).

It will be apparent that if a recombination occurs between homologous sequences of DNA from the two expression cassettes leading to deletion of the intervening sequence that sequence must comprise either the origin of replication or the sequence required for plasmid replication (in which case the plasmid will not replicate further) or the gene giving the selective advantage in which case the plasmid will tend to be lost by selection. Such losses however will be less than those occurring in plasmids with inverted repeat sequences in addition to the genes.

Surprisingly we have found that in the case of plasmids in which the expression cassettes are close together, for example separated by at most 5 kB and preferably at most 2 kB (as judged by the separation of their closest points) if one of the cassettes is deleted the resulting plasmid is at a selective disadvantage and therefore the microbes containing plasmids with both active cassettes continue to predominate until simultaneous inactivation of both cassettes occurs.

In a further form of the invention the genes for producing the desired protein are arranged to read in the opposite sense in the plasmid, i.e. if one is regarded as clockwise the other is anticlockwise. This makes it difficult for homologous sequences to come into contact, especially if the genes are close together, in a "head-to-head" or "tail-to-tail" relationship with as little DNA between them as possible.

The invention also comprises microbes containing plasmids according to the invention and also processes in which a desired protein is produced by means of such plasmids and/or microbes. The protein may be separated therefrom for example in a purified form if desired.

The invention also comprises a process in which a plasmid is cut at a first restriction site, a desired expression cassette is inserted at the first restriction site to form a modified plasmid, the modified plasmid is cut at a second restriction site which is not homologous with the first restriction site and a desired expression cassette is inserted at the second restriction site, the first and second restriction sites being separated on one side by a sequence which comprises an origin of replication and if they are not separated on the other side by a sequence which includes a gene giving a selective advantage to the host organism or a sequence required for plasmid replication, such a gene is inserted on that side, the plasmid being substantially free from inverted repeat sequences other than sequences represented by the expression cassette.

Preferably the host has a recombinational deficiency. The deficiency may be in consequence of the non-functionality or deletion of a recombination gene, for example rec A or preferably rec J gene.

DETAILED DESCRIPTION OF THE INVENTION

Increased Stability of Xylanase Expressing Plasmid In Continuous Culture

Figure 1:
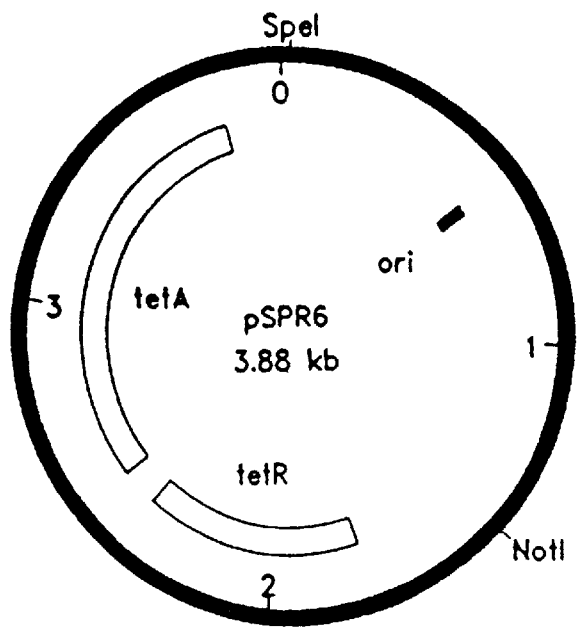
FIG. 1: Plasmid pSPR6.

Plasmid pSPR6 (see FIG. 1), (in *Escherichia coli* NM554 host NCIMB 40786 deposited with The National Collections of Industrial and Marine Bacteria Limited, 23 St Machar Drive, Aberdeen AB2 1RY Scotland UK on Feb. 8, 1996 under the Budapest Treaty) contains unique NotI and SpeI restriction sites which are positioned on either side of the plasmid origin of replication (ori) and on either side of a tetracycline resistance marker tetA/R. This plasmid allows the insertion of two independent copies of an expression cassette to improve the genetic stability of the plasmid during fermentations.

In this example the expression cassette was DNA encoding the expression of a fungal xylanase comprising of a constitutive promoter (gene A3 promoter from bacteriophage T7), a ribosome binding site (from lac z of *E.coli*), the coding sequence for the enzyme (truncated xylanase gene from plasmid pNX10 described in WO 93/25693) and a transcriptional terminator from bacteriophage T4. The expression cassette was flanked by either NotI or SpeI restriction sites. The expression cassette can be obtained by complete digestion of the plasmid pSPR8 in *E. coli* NM554, (NCIMB 40787 deposited with The National Collections of Industrial and Marine Bacteria Limited, 23 St Machar Drive, Aberdeen AB2 1RY Scotland UK on Feb. 8, 1996 under the Budapest Treaty) using restriction endonucleases NotI or SpeI in a high salt restriction buffer.

Strain *E.coli* NM554 (pSPR8) was constructed as follows: Plasmid DNA was prepared from *E. coli* strain NM554 (pSPR6) grown overnight at 37° C. in L broth (1% tryptone, 0.5% yeast extract, 0.5% NaCl) using "Rapid Pure Miniprep" (RPM) (Stratech Scientific Ltd, Luton, UK) following the manufacturers protocol. Plasmid DNA may also be isolated using standard methods such as described by Sambrook et al[1]. 50 μl of plasmid pSPR6 DNA was digested with restriction endonuclease NotI (Boehringer Mannheim, Lewes, UK) with the addition of 6 μl of the manufacturers H buffer (high salt restriction buffer) and 20 units of restriction enzyme. Digestion was carried out at 37° C. for 16 h.

The xylanase expression cassette was digested with NotI and ligated to plasmid pSPR6 similarly digested with NotI, as follows. The two species of DNA were mixed and the restriction enzyme and other contaminants were removed using an RPM miniprep (following the manufacturer's protocol but with the following modifications: DNA mixture used in place of cleared lysate and DNA eluted into 40 μl). 0.5 μl of 100 mM adenosine triphosphate (ATP) was added with 4 μl of M buffer (medium salt restriction buffer). 1 unit of T4 DNA ligase (Boehringer Mannheim) was added and the reaction incubated at 18° C. for 16 h.

5 μl of the ligation reaction was mixed with 100 μl of E.coli strain JM109 (ATCC 53323) competent cell suspension, produced by calcium chloride treatment essentially as described by Hanahan[2], and incubated on ice for 45 m. Cells were then heat shocked at 42° C. for 90 s and returned to ice for 2 m. 1 ml of L broth was added and cells incubated at 37° C., with shaking, for 1 h before plating out dilutions onto L agar plates (L broth+1% bacteriological agar) containing 10 μg/ml tetracycline and 1% remazol brilliant blue—xylan (RBB-Xylan, Sigma, Poole, UK). Plates were incubated for 24 h at 37° C. One colony which gave a zone of clearing and contained the expected plasmid when miniprep DNA was digested with NotI was designated JM109 (pSPR7).

Figure 2:
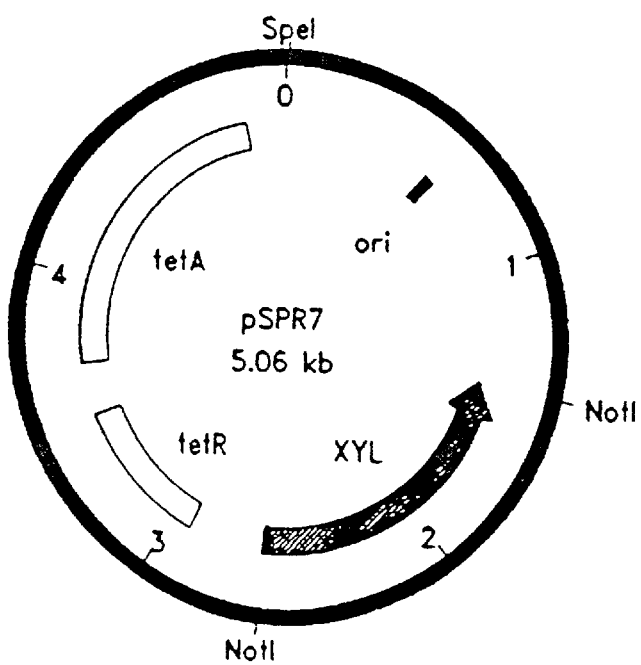
FIG. 2: Plasmid pSPR7.

Plasmid DNA from pSPR7 which is shown diagramatically in FIG. 2 was prepared as above from an overnight culture of JM109 (pSPR7) in L broth supplemented with 10 μg/ml tetracycline. 50 μl of plasmid DNA was linearised by digestion with restriction endonuclease SpeI (Boehringer Mannheim) by adding 5 μl of manufacturers H buffer and 20 units of SpeI enzyme. Reaction was incubated for 16 h at 37° C. The position of the NotI flanked xylanase expression cassette (XYL) relative to the plasmid origin of replication (ori) and the selectable marker (tetA/R) is shown.

A second xylanase expression cassette, identical to the first except flanked by SpeI restriction sites rather than NotI, was digested with SpeI as described above. This expression cassette may be obtained by the complete digestion of plasmid pSPR8 with the restriction enzyme SpeI. This DNA was ligated to SpeI digested plasmid pSPR7 exactly as described above but with selection of transformants on L agar containing 10 μg/ml tetracycline.

Figure 3:
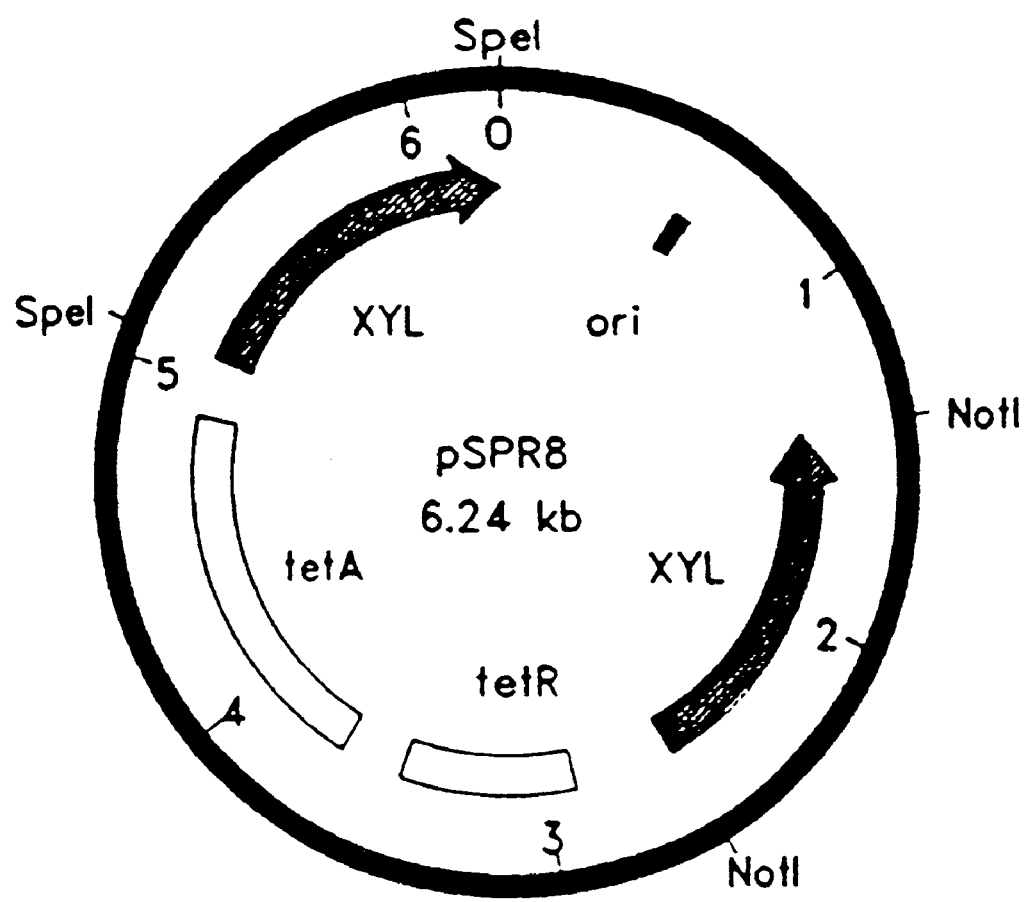
FIG. 3: Plasmid pSPR8.

Tetracycline resistant colonies were screened using a rapid lysis method (Twigg and Sherrett[3]) to estimate the size of the plasmid carried. 1 colony which contained a plasmid larger than plasmid pSPR7 and which subsequent digests of isolated plasmid DNA with NotI and SpeI restriction endonucleases showed to contain 2 copies of the xylanase expression cassette was designated JM109 (pSPR8), see FIG. 3 which shows plasmid pSPR8 showing the positions of both inserted xylanase expression cassettes (XYL) relative to the plasmid origin of replication (ori) and selectable marker (tetA/R).

Plasmid DNA was prepared from JM109 (pSPR8) and JM109 (pSPR7) and 1 μl used to transform E. coli strain NM554 (Stratagene, Cambridge, UK). Preparation of DNA and competent cells and transformation of DNA were done as described above. Transformants were selected on L agar containing 10 μg/ml tetracycline. Stocks of NM554 (pSPR7) and NM554 (pSPR8) were stored at −70° C. in L broth containing 10 μg/ml tetracycline and 25% (v/v) glycerol.

To prepare a fermentation inoculum, 50 ml of L broth containing 10 μg/ml tetracycline was inoculated with 500 μl from freezer stock and grown for approximately 4 h at 37° C. with rapid aeration before transfer to the fermenter.

Fermentations were done using Braun ED/ER5 fermenters (B. Braun Biotech, Reading, UK). Vessels were in situ sterilised and bottom agitated using 2×70 mm diameter Rushton impellers. The fermenter working volume was approximately 2 L. The medium used throughout the experiments was JV1 (see appendix). Temperature was maintained at 37° C.±0.2° C. The pH was measured using an Ingold pH probe and maintained at 6.7±0.1 by the controlled addition of filter sterilised 10M $NH_4OH$ and 2M $H_3PO_4$. An agitation speed of 600 rpm was used with air or 35% $O_2$ aeration to maintain a %$pO_2$ (dissolved oxygen tension) between 20% and 80%, of saturation measured by an Ingold oxygen probe. Foaming was controlled by the addition of sterile Diamond Shamrock PPG Foamaster EEA 142 at a rate of 0.1 ml/h.

50 ml inoculum was transferred to the fermenter which contained 2 L of JV1 medium plus 30 g/l glycerol and 10 ppm $Fe^{2+}$ (as $FeSO_4.7H_2O$). Cultures were allowed to grow in batch to a point at which the $CO_2$ evolution rate was between 10 and 40 mM/l/h (typically 20 mM $CO_2$/l/h), when the fermenter was switched to continuous operation at a dilution rate of 0.1 $h^{-1}$. JV1 medium was fed with separate feeds of sterile glycerol (feed rate 30 g/1) and $FeSO_4.7H_2O$ (feed rate 10 mg $Fe^{2+}$/l). 1 ml samples were regularly withdrawn and stored at −20° C. in 25% glycerol for later analysis of plasmid content. Enzyme activity and dry cell weight was also periodically measured in 10 ml samples. Xylanase enzyme activity was determined by measuring the amount of reducing sugar released from soluble oat spelt xylan substrate (1%), essentially as described by Kellett et al[4]. The production of xylanase and molecular weight was confirmed by sodium dodecyl sulphate polyacrylamide gel electrophoresis (SDS-PAGE) on an 8–25% gradient gel with commasie blue protein staining using Phast electrophoresis system (Pharmacia Biotech, St Albans, UK). Dry cell weights were determined by pelleting the cells in the withdrawn sample by centrifugation at 5700 rpm in a Beckman TJ-6 centrifuge for 20 m and resuspending cells in 2–3 mls Tris buffer (100 mM, pH7.2). Cells were then re-pelleted and dried in a pre-weighed tube in an oven at 105° C. for 16 h and mass of dried cells determined.

Changes to plasmid size during the fermentations were detected by plating of stored fermentation samples onto L agar containing 10 μg/ml tetracycline and 1% RBB-Xylan. Colonies were then picked and lysed using the procedure described by Twigg and Sherrett[3]. Changes in plasmid size were seen as a shift in mobility of the plasmid band on a 1% agarose gel compared to the control plasmid (agarose gel electrophoresis was done as described by Sambrook et al[1]).

Figure 4:
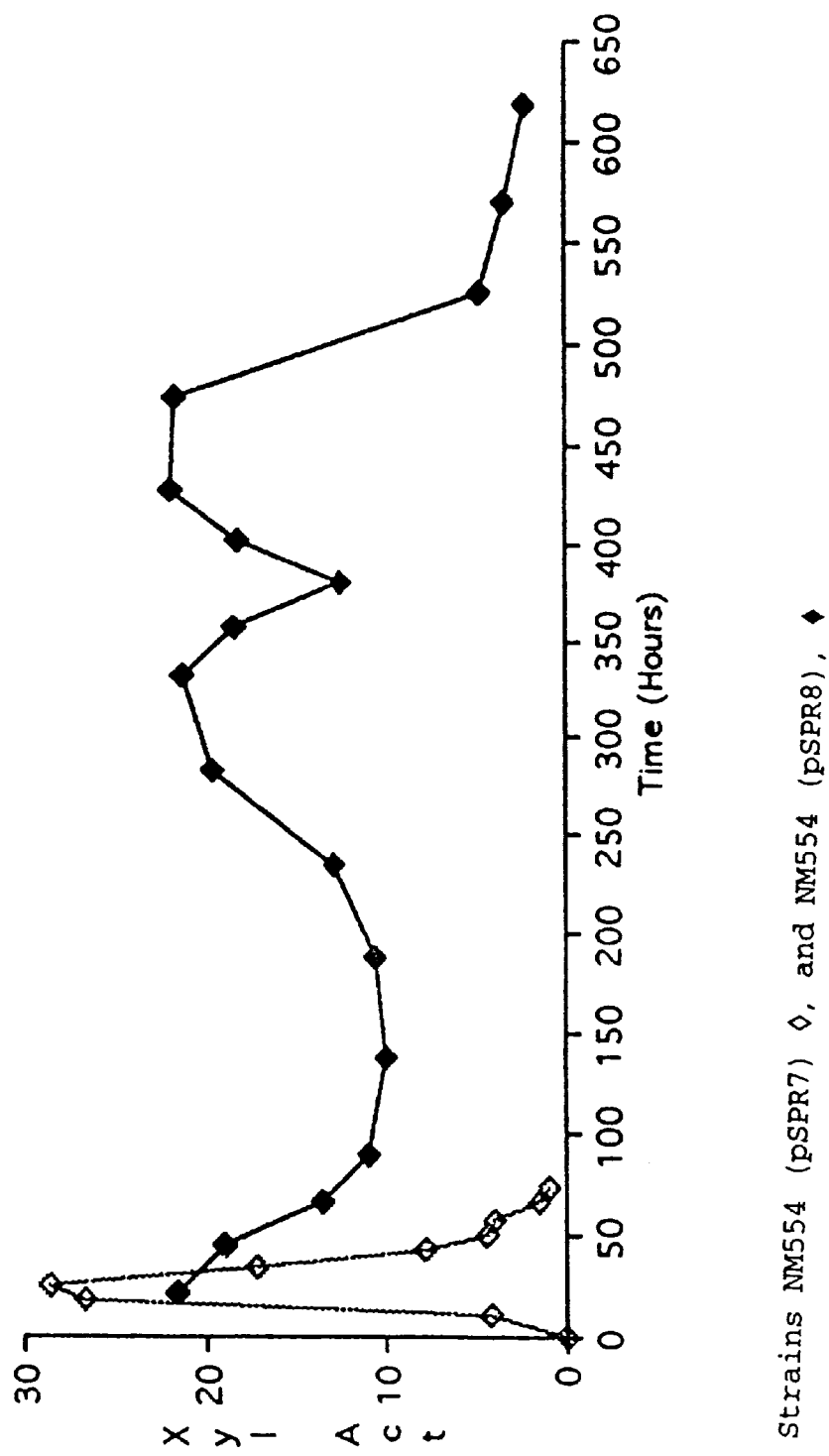
FIG. 4: Xylanase activities (KU/ml) for fermentations of *E. coli* strains NM554 (pSPR7) (open symbols) and NM554 (pSPR8) (filled symbols).

FIG. 4 shows xylanase activities (KU/ml) for fermentations of E.coli strains NM554 (pSPR7) ◊, and NM554 (pSPR8), ♦, growing in JV1 medium. Cultures switched from batch to continuous culture, with dilution rate of 0.1 $h^{-1}$, at approx. 10 hrs. These results show that strain NM554 (pSPR7), with a single copy of the xylanase expression cassette, very rapidly lost enzyme activity during continuous culture. SDS PAGE analysis of samples confirmed that the loss of enzyme activity corresponded to the loss of production of a heterologous protein band. Examination of plasmids using the rapid lysis technique showed no difference in plasmid size compared to pSPR7 control in samples taken up to 19 hrs, but showed several differently sized plasmids at the 50 hr and 72 hr sample points, indicating rearrangements and deletions had occurred in this plasmid causing the loss of enzyme activity.

Strain NM554 (pSPR8), containing 2 copies of the xylanase expression cassette, produced a high level of xylanase activity for 480 hrs in continuous culture. SDS PAGE confirmed production of heterologous protein over this time period. Analysis of plasmids from fermentation samples showed no detectable change in plasmid size during the course of this experiment, indicated that no rearrangements or deletions had occurred.

It was noted that the peak xylanase activity for NM554 (pSPR7) was higher than for NM554 (pSPR8) when the continuous fermentation was operated at a dilution rate of 0.1 h$^{-1}$. In order to investigate whether the observed increase in strain stability was due to this initial reduction in enzyme expression strain NM554 (pSPR7) was fermented as previously but with a dilution rate of 0.2 h$^{-1}$. This had the effect of reducing the peak xylanase activity to a comparable level to that seen with strain NM554 (pSPRs) operated at a dilution rate of 0.1 h$^{-1}$. Results showed the same instability despite the reduced expression level. Analysis of plasmid content showed changes in plasmid size similar to those seen previously.

Increased Stability of Dehalogenase Expressing Plasmid in Continuous Culture

The invention was further exemplified through production of a second protein, a haloalkanoic acid dehalogenase. In this example the host strain, promoter, ribosomal binding site, structural gene and fermentation medium were all different from those used in the xylanase example indicating the wide applicability of the invention.

Plasmid pSPR6 was modified to remove the unique NotI restriction site and introduce a unique PstI restriction site at the same position. Plasmid pSPR6 DNA was isolated and digested with NotI restriction enzyme, as above. Approx 2 μg of a synthetic oligonucleotide with the sequence GGC-CCTGCAG (SEQ ID NO: 1) was self annealed by heating to 94° C. in high salt restriction buffer and cooling slowly to room temperature. The annealed oligonucleotide and digested pSPR6 DNA were mixed, ATP added to final concentration of 1 mM and 1 unit of T4 DNA ligase added. Reaction was incubated at 18° C. overnight. Ligation mix was transformed into JM109 competent cells as described above and plated onto L agar plates containing 10 μg/ml tetracycline. Randomly picked colonies were screened by isolating plasmid DNA and digesting with Not I and PstI restriction enzymes in separate reactions. One clone which failed to digest with NotI but digested with PstI was isolated and designated JM109 (pSPR6pst).

Plasmid pSPR6pst DNA was isolated and digested with PstI restriction enzyme in high salt restriction buffer. After 3 h incubation at 37° C. 1 unit of calf intestinal alkaline phosphatase (Boehringer Mannheim) was added to prevent relegation. The reaction was incubated at 37° C. for a further 30 mins then stopped by adding EDTA to a final concentration of 5 mM and heating the reaction to 75° C. for 10 mins.

The dehalogenase expression cassette, comprising the E. coli trp promoter, a two cistron type ribosomal binding site (Gold and Stormo[5]), the hadD dehalogenase structural gene (Barth et al[6].,) and T4 phage transcriptional terminator, may be obtained by digesting the plasmid pSPR11.1 (deposited in E.coli host strain XL1 Blue MR at NCIMB as deposit no 40859 on Feb. 12, 1997) with the restriction enzyme PstI as described above. Plasmid pSPR10, which contains a single copy of the dehalogenase expression cassette, may then be obtained by ligation of this DNA with the pSPR6pst DNA prepared as above, selecting for transformants on Lagar containing 10 μg/ml of tetracycline.

Plasmid pSPR11.1 (available from NCIMB in host strain XL1 Blue MR, deposit no 40859), contains 2 copies of the same dehalogenase expression cassette. This plasmid was constructed by the addition of a second copy of the expression cassette into a unique SwaI restriction site on plasmid pSPR10. Plasmid pSPR10 DNA was isolated as previously and digested with restriction enzyme SwaI in high salt restriction buffer before treatment with calf intestinal alkaline phosphatase as described above. The dehalogenase expression cassette may be obtained by digestion of pSPR11.1 with restriction enzyme PstI. To produce blunt ended DNA compatible with the SwaI digested plasmid pSPR10, 1 unit of T4 DNA polymerase (Boehringer Mannheim) and a final concentration of 200 μM each deoxyadenosine 5' triphosphate, deoxy-cytidine 5' triphosphate deoxyguanosine 5' triphosphate and thymidine 5' triphosphate (all from Boehringer Mannheim) was added to the reaction after 3 h incubation and incubated a further 30 mins at 12° C. The reaction was stopped by heating to 75° C. for 10 mins. The blunt ended dehalogenase expression cassette and SwaI digested pSPR10 were ligated and transformed into XL1 Blue MR competent cells (Stratagene) as described above and plated onto L agar plates containing 10 μg/ml tetracycline. Plasmid pSPR11.1 was identified by restriction digests of isolated plasmid DNA, as containing 2 copies of the expression cassette in opposite orientations to one another.

Fermentation experiments were conducted in a derivative of E.coli strain W3110 (ATCC 27325)(American Type Culture Collection (ATCC), 10801 University Blvd, Manassas, Va., 20110-2209, USA) engineered to be recombinationally deficient due to a deletion of the recJ gene. The construction of this strain is given, but other recombinationally deficient hosts may also be used. 2 PCR products were produced of regions of the E.coli chromosome flanking the recJ gene, primers used were:

CTGGATCCCGGCGTTTTCAGGCTTTGCTC (SEQ ID NO: 2) with ACAGATCTTCACCGACCACAATAATC-CGC (SEQ ID NO: 3) to give product 1 and ACAGATCT-TGACCCTGTGCGAGAAACTGG (SEQ ID NO: 4) with TGGGATCCGCTCGGCGTTTACTTCTTCCA (SEQ ID NO: 5) to give product 2. PCR reactions were carried out using 35 cycles of denaturation at 94° C. for 1 min; prime annealing at 60° C. per 1 min and product extension at 72° C. per 1 min. Reactions were performed in a volume of 100 μl, containing 200 μM of each nucleoside triphosphate. Taq DNA polymerase buffer (Promega, Southampton;) and 5 units of Taq DNA polymerase. E.coli W3110 cells were used as template DNA. The 2 PCR products produced were purified using an RPM column, as above, and cloned using the pMOS blue T vector kit (Amersham, Amersham, UK) following the manufacturers protocol.

Plasmid containing PCR product 1 was isolated and digested with restriction enzyme BglII (Boehringer Mannheim) in medium salt restriction buffer. A DNA fragment encoding streptomycin and spectinomycin resistance was produced by Bam HI restriction digestion of plasmid pUT::miniTn5Sm/Sp (De Lorenzo[7]) in medium salt restriction buffer. This fragment was ligated to the digested plasmid and transformed into XL1 Blue MR competent cells with selection for transformants on L agar containing 50 μg/ml ampicillin and 25 μg/ml streptomycin. The insert from this plasmid was released by restriction digestion with the enzyme BamHI in medium salt restriction buffer. This fragment was ligated to the plasmid containing PCR product 2 which was digested with the restriction enzyme BglII. Ligation and transformation was as above. A clone was identified by restriction digestion of isolated plasmid DNA in which the streptomycin/spectinomycin resistance gene was flanked by DNA which normally flanks the recJ gene on the E.coli chromosome.

The deletion of the recJ gene on the E.coli chromosome was achieved by transformation of E.coli strain JC7623

(ATCC 47002). The above plasmid was digested using the restriction enzyme BamHI and the DNA concentrated by ethanol precipitation (Sambrook et al[1]) to give a final concentration approx 500 ng/ul. Fresh electrocompetent JC7623 cells were produced (Sambrook et al[1]) and 2 µl of digested plasmid DNA was transformed by electroporation in Gene Pulser Electroporation apparatus (Bio-Rad, Hemel Hempstead, UK) (15 KV/cm, 25 µF capacitance, 2000 parallel resistance). After a 2 hr recovery period shaking in L broth at 37° C., transformants were recovered on L agar containing 25 µg/ml streptomycin and 25 µg/ml spectinomycin. Transformants were screened for sensitivity to ampicillin by plating onto L agar containing 100 µg/ml ampicillin. A transformant was identified as resistant to streptomycin and spectinomycin but sensitive to ampicillin and with an increased sensitivity to UV light compared to strain JC7623. This strain was designated JC7623 ΔrecJ.

The ΔrecJ mutation was introduced to strain W3110 by P1 phage transduction. A phage lysate was raised on JC7623 and used to infect W3110 using the method described by Miller[8]. Transductants were selected on L agar containing streptomycin and spectinomycin as above.

For fermentations the strain W3110 ΔrecJ was transformed with the plasmids pSPR10 and pSPR11.1 using electroporation as described above.

Fermentation inocula and fermentations of dehalogenase producing strains were carried out essentially as described for xylanase production except that no yeast autolysate was present in the medium and glucose was used rather than glycerol.

Dehalogenase enzyme activity was measured as the rate of dechlorination of 2-chloropropionic acid, (Fluka Chemical, Gillingham, Dorset, UK) neutralised with NaOH.

Figure 5:
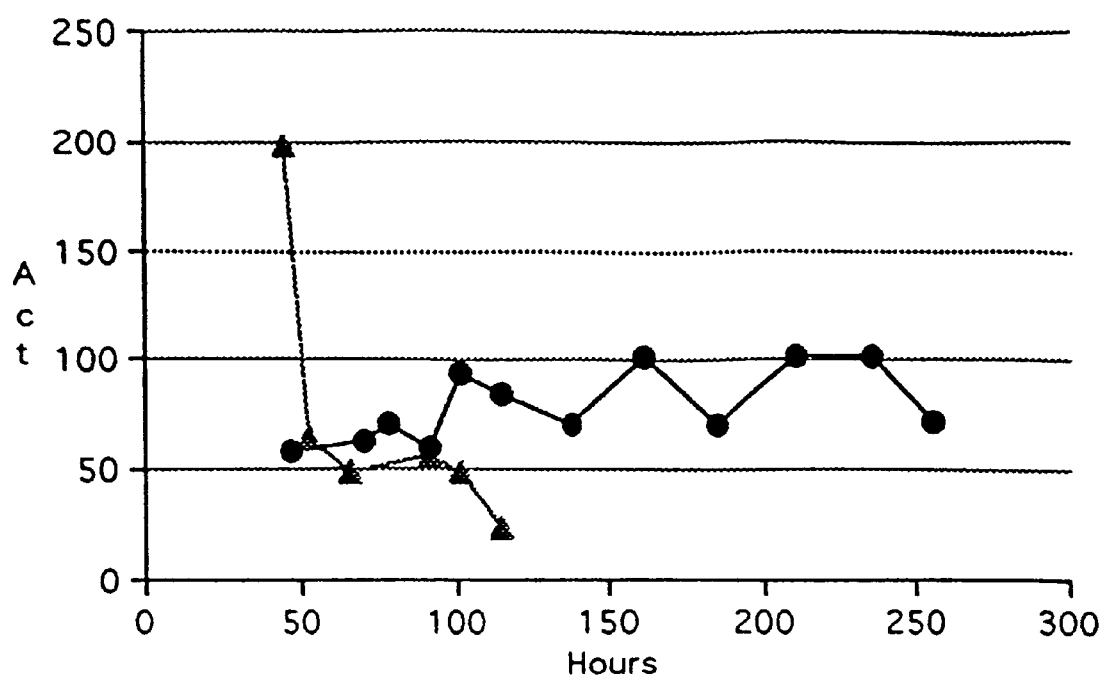
FIG. 5: Dehalogenase activities (Units/ml) for fermentations of *E. coli* strains W3110 ΔrecJ (pSPR10)(triangles) and W3110 ΔrecJ (pSPR11.1) (circles).

Results of continuous fermentations of W3110 ΔrecJ (pSPR10) and W3110 ΔrecJ (pSPR11.1) are shown in FIG. 5. They show dehalogenase activities (Units/ml) for fermentations of *E.coli* strains W3110 ΔrecJ (pSPR10) ▲ and W3110 ΔrecJ (pSPR11.1) ● growing in JV1 medium, modified as described. The cultures were switched from batch to continuous operation, with dilution rate of 0.1 h$^{-1}$, at approx 40 hrs. It can clearly be seen that the strain with pSPR11.1, containing 2 copies of the dehalogenase expression cassette, has much greater stability than the strain with plasmid pSPR10, which has only a single copy of the expression cassette. It is clear that although the peak enzyme activity is reduced the overall productivity of the fermentation is greatly enhanced.

APPENDIX

| Fermentation Medium (JV1) | |
|---|---|
| $K_2SO_4$ | 2 g/l |
| $MgSO_4.7H_2O$ | 1.5 g/l |
| $H_3PO_4$ (85%) | 0.14 ml/l |
| $CaCl_2.2H_2O$ | 0.11 g/l |

APPENDIX-continued

| Fermentation Medium (JV1) | |
|---|---|
| Trace Elements Solution | 1 ml/l |
| Yeast autolysate (Biospringer, Low Salt, Grade D,) | 20 g/l |
| Thiamine HCl (Sigma Chemicals, UK 32 g/l sterile stock) | 0.5 ml/l |
| Tetracycline hydrochloride (Sigma Chemicals, UK 67 mg/ml sterile stock) | 0.15 ml/l |

Trace Element Solution contained 0.2 g/l $AlCl_3.6H_2O$, 0.08 g/l $CoCl_2.6H_2O$, 0.02 g/l $CuCl_2.2H_2O$, 0.01 g/l $H_3BO_4$, 0.2 g/l KI, 0.5 g/l $MnSO_4.H_2O$, 0.01 g/l $NiSO_4.6H_2O$, 0.5 g/l $Na_2MO_4.2H_2O$, 0.5 g/l $ZnSO_4.7H_4O$.

All chemicals were of "AR" grade and obtained from Fisons (Loughbrough, UK) unless otherwise stated. Sterilisation was carried out at 121° C. for 30 m. Thiamine, trace elements and tetracycline solutions were filter sterilised through a 0.2 µm filter and added aseptically.

REFERENCES

1. Sambrook, J., E. F. Fritsch and T. Maniatis. 1989. Molecular Cloning, A Laboratory Manual. Cold Spring Harbor Laboratory Press, New York.

2. Hanahan, D. 1985. Techniques for transformation of *Escherichia coli*. In: DNA Cloning vol, A Practical Approach (Ed: D. M. G. Glover) pp 109–135. IRL Press, Oxford.

3. Twigg, A. T. and D. Sherratt. 1980. Trans-complementable copy number mutants of plasmid ColE1. Nature 283 pp 216–218.

4. Kellet, L. E., D. M. Poole, L. M. A. Ferreira, A. J. Durrant, G. P. Hazelwood and H. J. Gilbert. 1990. Xylanase B and an arabinofuranosidase from Pseudomonas fluorescens subsp. cellulosa contain identical cellulose-binding domains and are encoded by adjacent genes. Biochem J 272 pp 369–376.

5. Gold, L. and Stormo, G. D., 1990. High Level Translation Initiation. Methods in Enzymology 185 p 89–103.

6. Barth, P. T., Bolton, L., and Thomson J. C., 1992. Cloning and Partial Sequencing of an Operon Encoding Two Pseudomonas putida Haloalkanoate Dehalogenases of Opposite Stereospecificity. Journal of Bacteriology 174, p 2612–2619.

7. De Lorenzo, V., Herrero, M., Jakubzik, U. and Timmis, K. N. 1990. Mini-T-5 Transposon Derivatives for Insertion Mutagensis, Promoter Probing and Chromosomal Insertion of Cloned DNA in Gram Negative Eubacteria. Journal of Bacteriology. 172 p 6568–6571.

8. Miller, J. H. 1972. In: Experiments in Molecular Genetics, pp 201–205. Cold Spring Harbor Laboratory, New York.

What is claimed is:

1. In a continuous process for the fermentation of microbes containing plasmids or for the production of polypeptides expressed by genes of such plasmids, said process including the steps of culturing the microbes and recovering a product therefrom, the use of a plasmid which comprises (1) an origin of replication;

(2) a gene encoding a selectable marker or if an additional sequence is required for plasmid replication, such a sequence; and (3) two expression cassettes which code for the same polypeptides, each cassette being in a DNA sequence located between the origin of replication and a gene encoding a selectable marker or the additional sequence required for plasmid replication; but being separated from one another on one side by DNA comprising the origin of replication and on the other side by DNA comprising the gene encoding a selectable marker or the additional sequence required for plasmid replication.

2. The process as claimed in claim 1 in which the expression cassettes code for the same polypeptide.

3. The process as claimed in claim 2 in which genes for producing a desired protein are arranged in the opposite sense in the plasmid.

4. The process as claimed in claim 1 in which the host has a recombinational deficiency.

5. The process according to claim 1 in which the cassettes are separated by at most 5 kB as judged by the separation of their closest ends.

6. The process according to claim 5 in which the cassettes are separated by at most 2 kB.

7. A plasmid which comprises (1) an origin of replication;

(2) an additional sequence required for plasmid replication or a gene encoding a selectable marker; and (3) two expression cassettes which code for the same polypeptides each cassette being in a DNA sequence located between the origin of replication and a gene giving a selective advantage or the additional sequence required for plasmid replication; but being separated from one another on one side by DNA comprising the origin of replication and on the other side by DNA comprising the gene encoding a selectable marker or the additional sequence required for plasmid replication;

said plasmid being substantially free from inverted repeat sequences other than sequences represented by the expression cassettes.

8. The plasmid as claimed in claim 7 in which genes for producing a desired protein read in the opposite sense and have at most 5 kB of DNA between their closest ends.

9. The plasmid as claimed in claim 8 in which the genes have at most 2 kB of DNA between their closest ends.

10. The plasmids pSPR6, pSPR8 and pSPR11.1.

11. A process for constructing a plasmid in which a plasmid is cut at a first restriction site, a desired expression cassette is inserted at the first restriction site to form a modified plasmid, the modified plasmid is cut at a second restriction site which is not homologous with the first restriction site and an identical desired expression cassette is inserted at the second site, the first and second restriction sites being separated on one side by a sequence which comprises an origin of replication and if they are not separated on the other side by a sequence which includes a gene encoding a selectable marker advantage or a sequence required for plasmid replication, such a gene or sequence is inserted on that side, the plasmid being substantially free from inverted repeat sequences other than sequences represented by the expression cassettes.

12. A microbe which comprises a plasmid as claimed in claim 11.

13. The plasmid as claimed in claim 11 which has at most one antibiotic resistance gene.

14. The process as claimed in claim 1 in which the plasmid has at most one antibiotic resistance gene.

* * * * *